United States Patent
Souvie et al.

(10) Patent No.: US 7,479,569 B2
(45) Date of Patent: *Jan. 20, 2009

(54) PROCESS FOR THE SYNTHESIS OF (7-METHOXY-3,4-DIHYDRO-1-NAPHTHALENYL) ACETONITRILE AND ITS APPLICATION IN THE SYNTHESIS OF AGOMELATINE

(75) Inventors: Jean-Claude Souvie, Le Havre (FR); Isaac Gonzalez Blanco, Toledo (ES)

(73) Assignee: Les Laboratoires Servier, Courbevoie Cedex (FR)

( * ) Notice: Subject to any disclaimer, the term of this patent is extended or adjusted under 35 U.S.C. 154(b) by 681 days.

This patent is subject to a terminal disclaimer.

(21) Appl. No.: 11/051,869

(22) Filed: Feb. 4, 2005

(65) Prior Publication Data

US 2005/0182268 A1    Aug. 18, 2005

(30) Foreign Application Priority Data

Feb. 13, 2004 (FR) .................................. 04 01436

(51) Int. Cl.
*C07C 255/03* (2006.01)
(52) U.S. Cl. ...................................................... 558/351
(58) Field of Classification Search ................. 558/351
See application file for complete search history.

(56) References Cited

U.S. PATENT DOCUMENTS 3,931,188 A   1/1976  Douglas et al.
3,992,403 A   11/1976 Roebke
2005/0182267 A1*  8/2005  Souvie et al. ............... 558/351

FOREIGN PATENT DOCUMENTS

EP    0447285    9/1991

OTHER PUBLICATIONS

French Search Report for French Application No. 04.01436, Sep. 15, 2004.
European Search Report for European Application No. 05290309, May 20, 2005.
International Search Report for International Application No. PCT/FR2005/000324, Jun. 16, 2005.

* cited by examiner

*Primary Examiner*—James O. Wilson
*Assistant Examiner*—Ebenezer Sackey
(74) *Attorney, Agent, or Firm*—Hueschen and Sage

(57) ABSTRACT

A process for the industrial synthesis of the compound of formula (I)

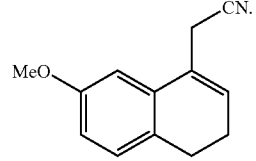

(I)

Application in the synthesis of agomelatine.

8 Claims, No Drawings

PROCESS FOR THE SYNTHESIS OF (7-METHOXY-3,4-DIHYDRO-1-NAPHTHALENYL) ACETONITRILE AND ITS APPLICATION IN THE SYNTHESIS OF AGOMELATINE

FIELD OF THE INVENTION

The present invention relates to a process for the industrial synthesis of (7-methoxy-3,4-dihydro-1-naphthalenyl)acetonitrile, and to its application in the industrial production of agomelatine, or N-[2-(7-methoxy-1-naphthyl)ethyl]acetamide.

More specifically, the present invention relates to a process for the industrial synthesis of the compound of formula (I):

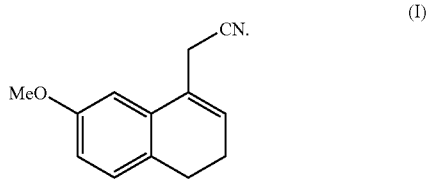

(I)

The compound of formula (I) obtained according to the process of the invention is useful in the synthesis of agomelatine, or N-[2-(7-methoxy-1-naphthyl)ethyl]acetamide, of formula (II):

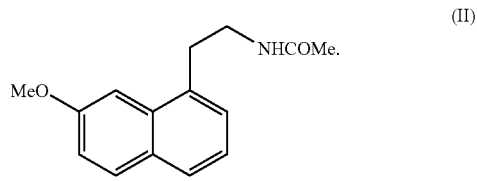

(II)

BACKGROUND OF THE INVENTION

Agomelatine, or N-[2-(7-methoxy-1-naphthyl)ethyl]acetamide, has valuable pharmaco-logical properties.

Indeed it has the double feature of being, on the one hand, an agonist of melatoninergic system receptors and, on the other hand, an antagonist of the 5-HT$_{2C}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting, from jetlag, appetite disorders and obesity.

DESCRIPTION OF THE PRIOR ART

Agomelatine, its preparation and its therapeutic use have been described in European Patent Specification EP 0 447 285.

In view of the pharmaceutical value of this compound, it has been important to be able to obtain it by an effective industrial synthesis process that is readily transposable to an industrial scale and that results in agomelatine in a good yield and with excellent purity.

Patent Specification EP 0 447 285 describes the preparation of agomelatine in eight steps, starting from 7-methoxy-1-tetralone, giving an average yield of less than 30%.

That process involves the action of ethyl bromoacetate, followed by aromatisation and saponification to yield the corresponding acid, which is then converted to acetamide and subsequently dehydrated to yield (7-methoxy-1-naphthyl)acetonitrile, this being followed by reduction, and then condensation of the acetyl chloride.

Transposition to an industrial scale has quickly demonstrated the difficulties of carrying out the process, these being caused principally by problems of reproducibility of the first step, which constitutes the action of ethyl bromoacetate on 7-methoxy-1-tetralone according to the Réformatsky reaction resulting in ethyl (7-methoxy-3,4-dihydro-1(2H)-naphthalenylidene)ethanoate.

Moreover, the subsequent step of aromatisation of ethyl (7-methoxy-3,4-dihydro-1(2H)-naphthalenylidene)ethanoate has in a mixture of products that is difficult to purify.

DETAILED DESCRIPTION OF THE INVENTION

The Applicant has now developed a new industrial synthesis process that results, in a reproducible manner and without the need for laborious purification, in agomelatine of a purity compatible with its use as a pharmaceutical active ingredient.

An alternative to the difficulties encountered with the process described in Patent Specification EP 0 447 285 has been obtained by directly condensing a cyano compound with 7-methoxy-1-tetralone. It was in addition necessary that the condensation compound obtained could readily be subjected to aromatisation to yield (7-methoxy-1-naphthyl)acetonitrile.

It is apparent that (7-methoxy-3,4-dihydro-1-naphthalenyl)acetonitrile would constitute an ideal synthesis intermediate that meets the requirements for direct synthesis from 7-methoxy-1-tetralone, and would be an excellent substrate for the aromatisation step.

Reactions for the direct condensation of tetralones with acetonitrile or acetonitrile compounds are described in the literature. In particular, Patent Specification U.S. Pat. No. 3,992,403 describes the condensation of cyanomethyl phosphonate with 6-fluoro-1-tetralone, and Patent Specification U.S. Pat. No. 3,931,188 describes the condensation of acetonitrile with tetralone leading to a cyano intermediate which is directly engaged in the subsequent reaction. Applied to 7-methoxy-1-tetralone, the condensation of acetonitrile yields a mixture of isomers in which "exo" constitutes the major portion and "endo" the minor portion, according to Figure 1:

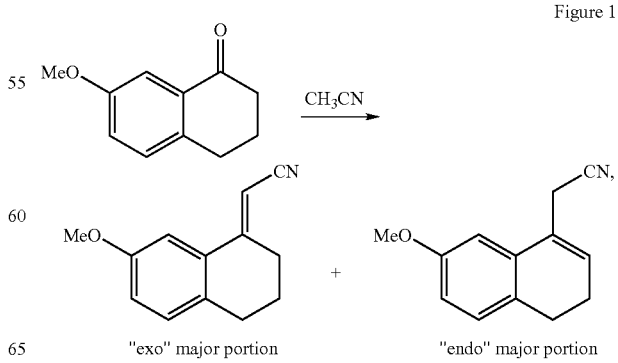

Figure 1 obtaining such a mixture requiring subsequent drastic aromatisation conditions that are not compatible with the industrial requirements for the purpose of carrying out the synthesis of agomelatine.

The Applicant has now developed a new industrial synthesis process that allows (7-methoxy-3,4-dihydro-1-naphthalenyl)acetonitrile to be obtained in a reproducible manner and without the need for laborious purification, especially free from the "exo" impurity of formula (III):

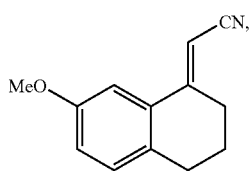
(III)

which impurity cannot be subjected to subsequent aromatisation under operating conditions that are compatible with the industrial requirements for the purpose of carrying out the synthesis of agomelatine.

More specifically, the present invention relates to a process for the industrial synthesis of the compound of formula (I):

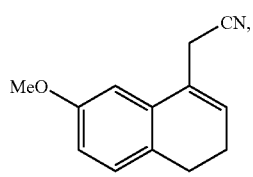
(I)

which is characterised in that 7-methoxy-1-tetralone of formula (IV):

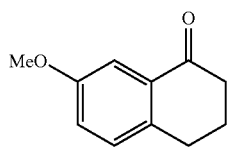
(IV)

is reacted with cyanoacetic acid of formula (V):

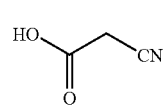
(V)

in conditions wherein the water formed is removed, in the presence of a catalytic amount of a compound of formula (VI):

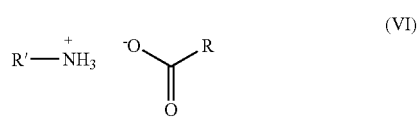
(VI)

wherein R and R', which may be the same or different, each represents a linear or branched ($C_3$-$C_{10}$)alkyl group, an unsubstituted or substituted aryl group, or an unsubstituted or substituted linear or branched aryl ($C_1$-$C_6$)alkyl group, to yield the compound of formula (I) after filtration and washing with a basic solution, which compound of formula (I) is isolated in the form of a solid after recrystallisation wherein:
aryl is understood to mean a phenyl, naphthyl or biphenyl group,
the term "substituted" governing the terms "aryl" and "arylalkyl" denotes that the aromatic moiety of those groups may be substituted by from 1 to 3 identical or different groups selected from linear or branched ($C_1$-$C_6$)alkyl, hydroxy and linear or branched ($C_1$-$C_6$)alkoxy.

More especially, the water formed during the reaction is removed by distillation. There is preferably used a reaction solvent that has a boiling temperature higher than or equal to that of water, and even more preferably that forms an azeotrope with water, such as, for example, xylene, toluene, anisole, ethylbenzene, tetrachloroethylene, cyclohexene or mesitylene.

Preferably, the reaction is carried out with reflux of toluene or xylene and, more especially, with reflux of toluene.

Advantageously one of the groups R or R' of the catalyst employed represents a linear or branched ($C_3$-$C_{10}$)alkyl group and the other represents an aryl or arylalkyl group. More especially, a preferred catalyst is that of formula (VI$_a$):

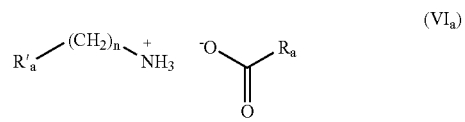
(VI$_a$)

wherein R'$_a$ represents a phenyl group unsubstituted or substituted by one or more linear or branched ($C_1$-$C_6$)alkyl groups, n is 0 or 1, and R$_a$ represents a linear ($C_3$-$C_{10}$)alkyl group.

Advantageously, R'$_a$ represents an unsubstituted or substituted phenyl group, more especially an unsubstituted phenyl group.

The preferred group R$_a$ is the hexyl group.

Advantageously, n is 1.

The preferred catalyst used in the process according to the invention is benzylammonium heptanoate of formula (VII):

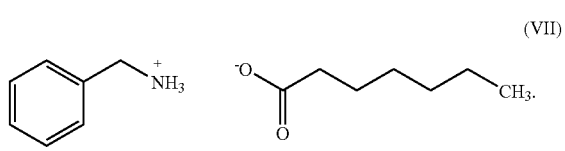
(VII)

Advantageously, the compound of formula (VI) is obtained after filtration and washing with a mineral or organic basic solution, such as NaOH, KOH, Ca(OH)$_2$, Sr(OH)$_2$ or NH$_4$OH, and more especially with a sodium hydroxide solution.

This process is of particular interest for the following reasons:

- it allows the "endo" compound, exclusively, to be obtained on an industrial scale. This result is altogether surprising considering the literature relating to that type of reaction, which most frequently reports obtaining "exo"/ "endo" mixtures (Tetrahedron, 1966, 22, 3021-3026). The result is due to the use of a compound of formula (VI) as reaction catalyst instead of the ammonium acetates currently used in such reactions (Bull. Soc. Chim. Fr., 1949, 884-890).
- the rate of conversion obtained is very high, exceeding 97%, unlike that which could be observed using acetic acid, for which the rate does not exceed 75%.

The compound of formula (I) so obtained is new and is useful as an intermediate in the synthesis of agomelatine, in which it is subjected to aromatisation followed by reduction and then to coupling with acetic anhydride.

The Examples below illustrate the invention but do not limit it in any way.

EXAMPLE 1

(7-Methoxy-3,4-dihydro-1-naphthalenyl)acetonitrile

There are introduced into a 670 litre reactor 85.0 kg of 7-methoxy-1-tetralone, 60.3 kg of cyanoacetic acid and 15.6 kg of heptanoic acid in toluene in the presence of 12.7 kg of benzylamine. The mixture is heated at reflux. When all the starting substrate has disappeared, the solution is cooled and filtered. The precipitate obtained is washed with toluene and then the filtrate obtained is washed with a 2N sodium hydroxide solution and subsequently with water until neutral. After removal of the solvent by evaporation, the resulting solid is recrystallised from an ethanol/water (80/20) mixture to give the title product in a yield of 90% and with a chemical purity exceeding 99%.

Melting point: 48-50° C.

EXAMPLE 2

(7-Methoxy-3,4-dihydro-1-naphthalenyl)acetonitrile

There are introduced into a 670 litre reactor 85.0 kg of 7-methoxy-1-tetralone, 60.3 kg of cyanoacetic acid and 15.6 kg of heptanoic acid in toluene in the presence of 11.0 kg of aniline. The mixture is heated at reflux. When all the starting substrate has disappeared, the solution is cooled and filtered. The precipitate obtained is washed with toluene and then the filtrate obtained is washed with a 2N sodium hydroxide solution and subsequently with water until neutral. After removal of the solvent by evaporation, the resulting solid is recrystallised from an ethanol/water (80/20) mixture to give the title product in a yield of 87% and with a chemical purity exceeding 99%.

Melting point 48-50° C.

We claim:

1. A process for the synthesis of a compound of formula (I)

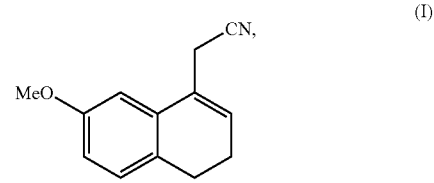

wherein 7-methoxy-1-tetralone of formula (IV):

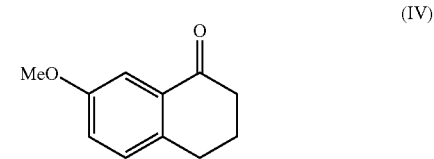

is reacted with cyanoacetic acid of formula (V):

under conditions wherein the water formed is removed, in the presence of a catalytic amount of a compound of formula (VI):

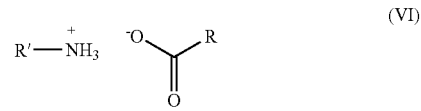

wherein R and R', which may be the same or different, each represents linear or branched (C$_3$-C$_{10}$)alkyl, unsubstituted or substituted aryl, or unsubstituted or substituted linear or branched aryl (C$_1$-C$_6$)alkyl, to yield the compound of formula (I) after filtration and washing with a basic solution, wherein the compound of formula (I) is isolated in the form of a solid after recrystallisation it being understood that:

aryl may be phenyl, naphthyl or biphenyl, the term "substituted" associated with the terms "aryl" and "arylalkyl" denotes that the aromatic moiety of those groups may be substituted by one or more, identical or different, groups selected from linear or branched (C$_1$-C$_6$)alkyl, hydroxy and linear or branched (C$_1$-C$_6$)alkoxy.

2. The process of claim 1, wherein the process is carried out in refluxing toluene.

3. The process of claim 1, wherein the compound of formula (VI) is selected from those of formula (VI$_a$):

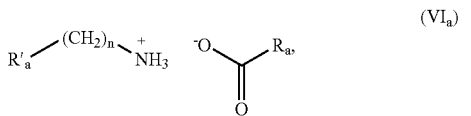

wherein R'$_a$ represents phenyl unsubstituted or substituted by one or more linear or branched (C$_1$-C$_6$)alkyl, n is 0 or 1, and R$_a$ represents linear (C$_3$-C$_{10}$)alkyl.

4. The process of claim 1, wherein R represents hexyl.

5. The process of claim 1, wherein R' represents benzyl.

6. The process of claim 1, wherein the compound of formula (VI) is benzylammonium heptanoate of formula (VII):

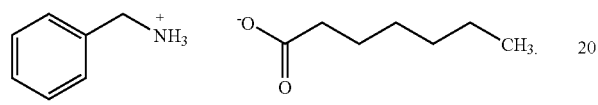

7. A compound of formula (I),

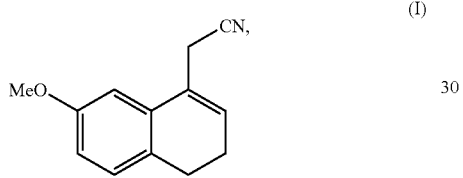

which is (7-methoxy-3,4-dihydro-1-naphthalenyl)acetonitrile, for use as an intermediate in the synthesis of agomelatine.

8. A process for the synthesis of agomelatine wherein 7-methoxy-1-tetralone of formula (IV):

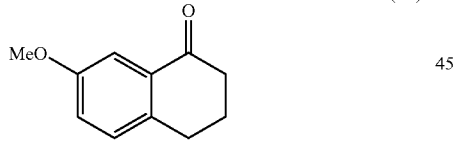

is reacted with cyanoacetic acid of formula (V):

under conditions wherein the water formed is removed, in the presence of a catalytic amount of a compound of formula (VI):

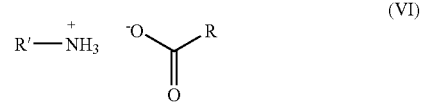

wherein R and R', which may be the same or different, each represents linear or branched (C$_3$-C$_{10}$)alkyl, unsubstituted or substituted aryl, or unsubstituted or substituted linear or branched aryl (C$_1$-C$_6$)alkyl, to yield the compound of formula (I) after filtration and washing with a basic solution, wherein the compound of formula (I) is isolated in the form of a solid after recrystallisation it being understood that:

aryl may be phenyl, naphthyl or biphenyl, the term "substituted" associated with the terms "aryl" and "arylalkyl" denotes that the aromatic moiety of those groups may be substituted by one or more, identical or different, groups selected from linear or branched (C$_1$-C$_6$)alkyl, hydroxy and linear or branched (C$_1$-C$_6$) alkoxy, which compound of formula (I) is subjected to aromatisation followed by reduction and then to coupling with acetic anhydride to yield agomelatine.

\* \* \* \* \*